(12) United States Patent
Wünsch et al.

(10) Patent No.: US 6,284,851 B1
(45) Date of Patent: Sep. 4, 2001

(54) CYCLOPENTA[I] PHENANTHRENE-METAL COMPLEX CATALYST SYSTEMS

(75) Inventors: Josef Wünsch, Schifferstadt (DE); Hans-Herbert Brintzinger, Taegerswilen (CH); Nicole Schneider; Marc Prosenc, both of Constance (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/445,699

(22) PCT Filed: Jun. 5, 1998

(86) PCT No.: PCT/EP98/03370
§ 371 Date: Dec. 13, 1999
§ 102(e) Date: Dec. 13, 1999

(87) PCT Pub. No.: WO98/57995
PCT Pub. Date: Dec. 23, 1998

(30) Foreign Application Priority Data

Jun. 18, 1997 (DE) .............................. 197 25 647

(51) Int. Cl.⁷ ..................................... C08F 4/42
(52) U.S. Cl. ............... 526/160; 526/97; 526/131; 526/943; 526/127; 502/152; 556/11; 556/7
(58) Field of Search .................. 526/160, 943, 526/97, 131, 127; 502/152; 556/11, 7

(56) References Cited

U.S. PATENT DOCUMENTS 6,090,962 * 7/2000 Rosen ..................... 556/11

FOREIGN PATENT DOCUMENTS 195 09 785   9/1996 (DE).
WO 99/14221 * 3/1999 (WO).

OTHER PUBLICATIONS

J. Org. Chem. 1989,54, S.171–175, Eliasson et al.
Schneider et al., Organometallics, 16, 3413–3420, Jul. 22, 1997.*
Schneider et al.,, Journal of Organometallic Chemistry, 545–546, 291–295, Oct. 30, 1997.*

* cited by examiner

Primary Examiner—David W. Wu
Assistant Examiner—Ling-Siu Choi
(74) Attorney, Agent, or Firm—Keil & Weinkauf

(57) ABSTRACT

In a process for preparing polymers based on monomers having a C=C double bond by homopolymerization or copolymerization of these monomers in the presence of a catalyst system comprising a metallocene complex A) and a compound B) capable of forming metallocenium ions and, if desired, an organometallic compound of main group I, II or III of the Periodic Table of the Elements C), the metallocene complex A) used is a compound of the formula (I)

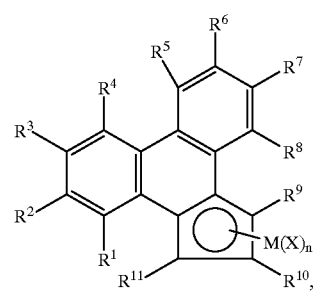

where the substituents and indices have the following meanings:

$R^1$ to $R^{11}$ are hydrogen, $C_1$–$C_{10}$-alkyl, 5- to 7-membered cycloalkyl which may in turn bear $C_1$–$C_6$-alkyl groups as substituents, $C_6$–$C_{15}$-aryl or arylalkyl, where two adjacent radicals $R^1$ to $R^8$ may together form a cyclic group having from 4 to 15 carbon atoms, or $Si(R^{12})_3$, where $R^{12}$ is $C_1$–$C_{10}$-alkyl, $C_6$–$C_{15}$-aryl or $C_3$–$C_{10}$-cycloalkyl, M is a metal of transition groups III to VI of the Periodic Table of the Elements or a metal of the lanthanide series, X are identical or different and are hydrogen, halogen, $C_1$–$C_{10}$-alkyl, $C_6$–$C_{15}$-aryl, $C_1$–$C_{10}$-alkoxy or $C_6$–$C_{15}$-aryloxy and n is 1, 2, 3, 4 or 5, where n corresponds to the valence of M minus 1.

8 Claims, No Drawings

US 6,284,851 B1

CYCLOPENTA[I] PHENANTHRENE-METAL COMPLEX CATALYST SYSTEMS

BACKGROUND AND BRIEF SUMMARY OF THE INVENTION

The present invention relates to a process for preparing polymers based on monomers having a C=C double bond by homopolymerization or copolymerization of these monomers in the presence of a catalyst system comprising a metallocene complex A) and a compound B) capable of forming metallocenium ions and, if desired, an organometallic compound of main group I, II or III of the Periodic Table of the Elements C), catalyst systems which are suitable for polymerizing monomers having a C=C double bond and comprise as active constituents A) a metallocene complex of the formula (I)

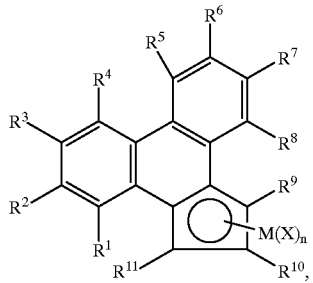

(I)

where the substituents and indices have the following meanings:

$R^1$ to $R^{11}$ are hydrogen, $C_1$–$C_{10}$-alkyl, 5- to 7-membered cycloalkyl which may in turn bear $C_1$–$C_6$-alkyl groups as substituents, $C_6$–$C_{15}$-aryl or arylalkyl, where two adjacent radicals $R^1$ to $R^8$ may together form a cyclic group having from 4 to 15 carbon atoms, or $Si(R^{12})_3$, where $R^{12}$ is $C_1$–$C_{10}$-alkyl, $C_6$–$C_{15}$-aryl or $C_3$–$C_{10}$-cycloalkyl, M is a metal of transition groups III to VI of the 40 Periodic Table of the Elements or a metal of the lanthanide series, X are identical or different and are hydrogen, halogen, $C_1$–$C_{10}$-alkyl, $C_6$–$C_{15}$-aryl, $C_1$–$C_{10}$-alkoxy or $C_6$–$C_{15}$-aryloxy and n is 1, 2, 3, 4 or 5, where n corresponds to the valence of M minus 1, B) a compound capable of forming metallocenium ions and, if desired, C) an organometallic compound of main group I, II or III of the Periodic Table of the Elements, metallocene complexes of the formula (I)

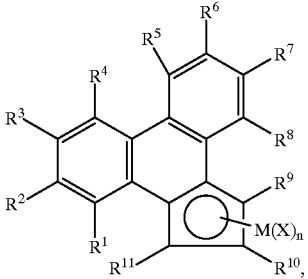

(I)

where the substituents and indices have the following meanings:

$R^1$ to $R^{11}$ are hydrogen, $C_1$–$C_{10}$-alkyl, 5- to 7-membered cycloalkyl which may in turn bear $C_1$–$C_6$-alkyl groups as substituents, $C_6$–$C_{15}$-aryl or arylalkyl, where two adjacent radicals $R^1$ to $R^8$ may together form a cyclic group having from 4 to 15 carbon atoms, or $Si(R^{12})_3$, where $R^{12}$ is $C_1$–$C_{10}$-alkyl, $C_6$–$C_{15}$-aryl or $C_3$–$C_{10}$-cycloalkyl, M is a metal of transition groups III to VI of the Periodic Table of the Elements or a metal of the lanthanide series, X are identical or different and are hydrogen, halogen, $C_1$–$C_{10}$-alkyl, $C_6$–$C_{15}$-aryl, $C_1$–$C_{10}$-alkoxy or $C_6$–$C_{15}$-aryloxy and n is 1, 2, 3, 4 or 5, where n corresponds to the valence of M minus 1.

The present invention further relates to polymers which are based on monomers having a C=C double bond and are obtainable by homopolymerization or copolymerization of these monomers in the presence of a catalyst system comprising a metallocene complex A) and a compound B) capable of forming metallocenium ions and, if desired, an organometallic compound of main group I, II or III of the Periodic Table of the Elements C), and also fibers, films and moldings comprising these polymers and the use of metallocene complexes (I) as components in catalyst systems or as catalysts.

Syndiotactic polymers of styrene are known. Owing to their property profile, eg. high hardness, high stiffness, dimensional stability and low dielectric constants, they can be used, for example, as electrical or mechanical components.

DETAILED DESCRIPTION OF THE INVENTION

It is an object of the present invention to find novel catalyst systems which can be used at relatively high polymerization temperatures, preferably above 60° C., have a high polymerization activity and give a polymer having a high proportion, preferably above 80% (determined by extraction of the crude polymer with n-butanone) of syndiotactic structural units and a high molecular weight $M_w$.

We have found that this object is achieved by a process for preparing polymers based on monomers having a C=C double bond by homopolymerization or copolymerization of these monomers in the presence of a catalyst system comprising a metallocene complex A) and a compound B) capable of forming metallocenium ions and, if desired, an organometallic compound of main group I, II or III of the Periodic Table of the Elements C), wherein the metallocene complex A) used is a compound of the formula (I)

(I)

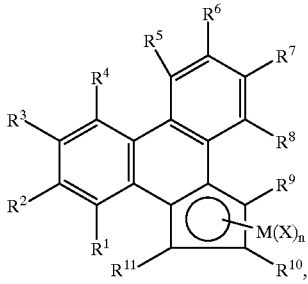

where the substituents and indices have the following meanings:

$R^1$ to $R^{11}$ are hydrogen, $C_1$–$C_{10}$-alkyl, 5- to 7-membered cycloalkyl which may in turn bear $C_1$–$C_6$-alkyl groups as substituents, $C_6$–$C_{15}$-aryl or arylalkyl, where two adjacent radicals $R^1$ to $R^8$ may together form a cyclic group having from 4 to 15 carbon atoms, or $Si(R^{12})_3$, where $R^{12}$ is $C_1$–$C_{10}$-alkyl, $C_6$–$C_{15}$-aryl or $C_3$–$C_{10}$-cycloalkyl, M is a metal of transition groups III to VI of the Periodic Table of the Elements or a metal of the lanthanide series X are identical or different and are hydrogen, halogen, $C_1$–$C_{10}$-alkyl, $C_6$–$C_{15}$-aryl, $C_1$–$C_{10}$-alkoxy or $C_6$–$C_{15}$-aryloxy and n is 1, 2, 3, 4 or 5, where n corresponds to the valence of M minus 1, by catalyst systems which are suitable for polymerizing monomers having a C=C double bond and comprise as active constituents A) a metallocene complex of the formula (I)

(I)

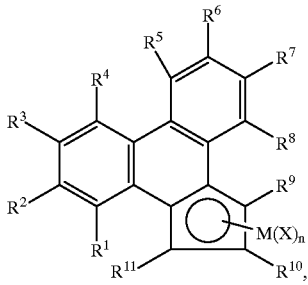

B) a compound capable of forming metallocenium ions and, if desired,

C) an organometallic compound of main group I, II or III of the Periodic Table of the Elements, by metallocene complexes of the formula (I)

(I)

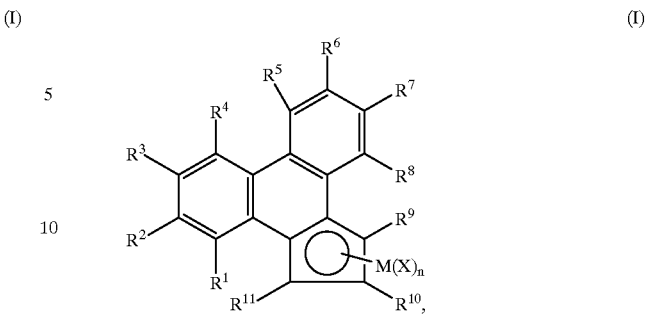

where the substituents and indices have the following meanings:

$R^1$ to $R^{11}$ are hydrogen, $C_1$–$C_{10}$-alkyl, 5- to 7-membered cycloalkyl which may in turn bear $C_1$–$C_6$-alkyl groups as substituents, $C_6$–$C_{15}$-aryl or arylalkyl, where two adjacent radicals $R^1$ to $R^8$ may together form a cyclic group having from 4 to 15 carbon atoms, or $Si(R^{12})_3$, where $R^{12}$ is $C_1$–$C_{10}$-alkyl, $C_6$–$C_{15}$-aryl or $C_3$–$C_{10}$-cycloalkyl, M is a metal of transition groups III to VI of the Periodic Table of the Elements or a metal of the lanthanide series, X are identical or different and are hydrogen, halogen, $C_1$–$C_{10}$-alkyl, $C_6$–$C_{15}$-aryl, $C_1$–$C_{10}$-alkoxy or $C_6$–$C_{15}$-aryloxy and n is 1, 2, 3, 4 or 5, where n corresponds to the valence of M minus 1, by polymers which are based on monomers having a C=C double bond and are obtainable by homopolymerization or copolymerization of these monomers in the presence of a catalyst system comprising a metallocene complex A), a compound B) capable of forming metallocenium ions and, if desired, an organometallic compound of main group I, II or III of the Periodic Table of the Elements C), wherein the metallocene complex A) used is a compound of the formula (I)

(I)

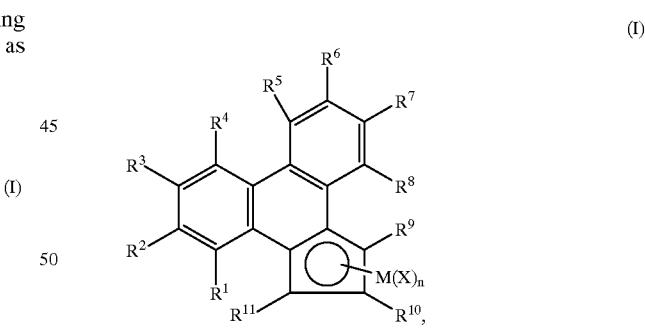

where the substituents and indices have the following meanings:

$R^1$ to $R^{11}$ are hydrogen, $C_1$–$C_{10}$-alkyl, 5- to 7-membered cycloalkyl which may in turn bear $C_1$–$C_6$-alkyl groups as substituents, $C_6$–$C_{15}$-aryl or arylalkyl, where two adjacent radicals $R^1$ to $R^8$ may together form a cyclic group having from 4 to 15 carbon atoms, or $Si(R^{12})_3$, where $R^{12}$ is $C_1$–$C_{10}$-alkyl, $C_6$–$C_{15}$-aryl or $C_3$–$C_{10}$-cycloalkyl, M is a metal of transition groups III to VI of the Periodic Table of the Elements or a metal of the lanthanide series, X are identical or different and are hydrogen, halogen, $C_1$–$C_{10}$-alkyl, $C_6$–$C_{15}$-aryl, $C_1$–$C_{10}$-alkoxy or $C_6$–$C_{15}$-aryloxy and n is 1, 2, 3, 4 or 5, where n corresponds to the valence of M minus 1, by fibers, films and moldings comprising the polymers of the present invention and also by the use of the metallocene complexes (I) of the present invention as components in catalyst systems or as catalysts.

Suitable monomers are generally all those which have a polymerizable carbon-carbon (C=C) double bond. Examples are linear alkenes having from 2 to 20 carbon atoms, where the double bond may be in an internal or terminal position, and cyclic or bicyclic alkenes having from 3 to 20 carbon atoms, where the C=C double bond can be in an endo or exo position. The linear and cyclic alkenes can be substituted by functional groups such as halogen, an ester group, a —COOH group or a nitrile group. Examples of such monomers are vinyl chloride, ethyl acrylate, methyl acrylate, methyl methacrylate and acrylonitrile. The linear and cyclic alkenes are preferably hydrocarbons without heteroatoms. Examples of such monomers are $C_2$–$C_{20}$-alk-1-enes such as ethylene, propylene, 1-butene, 1-hexene, 1-octene, 1-decene, cycloalkenes such as cyclopentene, cyclohexene, bicycloalkenes, such as norbornene and also dienes such as 1,3-butadiene, cyclopentadiene, norbornadiene. Preferred nonaromatic monomers are ethylene, propylene and 1,3-butadiene.

For the purposes of the present invention, preferred aromatic monomers are vinylaromatic compounds of the formula (II)

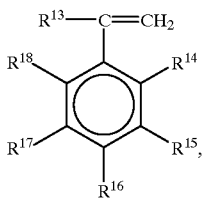

(II)

where the substituents have the following meanings:

$R^{13}$ is hydrogen or $C_1$–$C_4$-alkyl, $R^{14}$ to $R^{18}$ are, independently of one another, hydrogen, $C_1$–$C_{12}$-alkyl, $C_6$–$C_{18}$-aryl, halogen or two adjacent radicals together form a cyclic group having from 4 to 15 carbon atoms.

Preference is given to using vinylaromatic compounds of the formula II in which $R^{13}$ is hydrogen and $R^{14}$ to $R^1$ are hydrogen, $C_1$–$C_4$-alkyl, chlorine or phenyl or two adjacent radicals together form a cyclic group having from 4 to 12 carbon atoms, resulting in compounds of the formula II which are, for example, naphthalene derivatives or anthracene derivatives.

Examples of such preferred compounds II are: styrene, p-methylstyrene, p-chlorostyrene, 2,4-dimethylstyrene, 1,4-divinylbenzene, 4-vinylbiphenyl, 2-vinylnaphthalene and 9-vinylanthracene.

It is also possible to use mixtures of various vinylaromatic compounds II, but preference is given to using only one vinylaromatic compound.

Particularly preferred vinylaromatic compounds are styrene and p-methylstyrene.

The preparation of vinylaromatic compounds of the formula II is known per se and is described, for example, in Beilstein 5, 367, 474, 485.

Other monomers which can be used are branched monomers having at least two vinylaromatic functional radicals, for example tetrakis(4-vinylbenzyl)titanium or tetrakis(4-vinylbenzyl)silane. Further monomers of this type are described in the earlier German Patent Application 196 34 375.5-44.

In general, the monomers can also be used as a mixture. In this case, the mixing ratio is generally not critical.

The component A) of the catalyst system of the present invention is a metallocene complex of the formula (I)

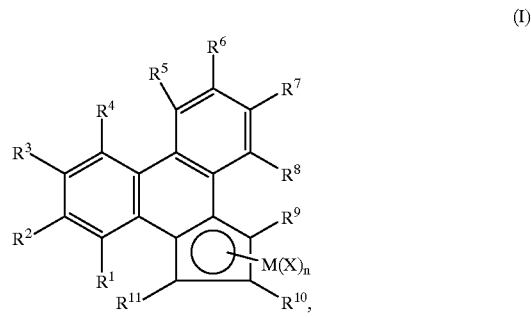

(I)

where the substituents and indices have the following meanings:

$R^1$ to $R^{11}$ are hydrogen, $C_1$–$C_{10}$-alkyl, 5- to 7-membered cycloalkyl which may in turn bear $C_1$–$C_6$-alkyl groups as substituents, $C_6$–$C_{15}$-aryl or arylalkyl, where two adjacent radicals $R^1$ to $R^8$ may together form a cyclic group having from 4 to 15 carbon atoms, or $Si(R^{12})_3$, where $R^{12}$ is $C_1$–$C_{10}$-alkyl, $C_6$–$C_{15}$-aryl or $C_3$–$C_{10}$-cycloalkyl, M is a metal of transition groups III to VI of the Periodic Table of the Elements or a metal of the lanthanide series, X are identical or different and are hydrogen, halogen, $C_1$–$C_{10}$-alkyl, $C_6$–$C_{15}$-aryl, $C_1$–$C_{10}$-alkoxy or $C_6$–$C_{15}$-aryloxy and n is 1, 2, 3, 4 or 5, where n corresponds to the valence of M minus 1.

Particularly preferred metallocene complexes of the formula I are those in which M is a metal of transition group IV of the Periodic Table of the Elements, in particular titanium, X is $C_1$–$C_{10}$-alkyl, $C_1$–$C_{10}$-alkoxy or halogen and n is 3.

Mixtures of various metallocene complexes can also be used.

Examples of metallocene complexes (I) according to the present invention are cyclopenta[l]phenanthrenetitanium trichloride, 2-methylcyclopenta[l]phenanthrenetitanium trichloride and 2-phenylcyclopenta[l]phenanthrenetitanium trichloride.

The synthesis of the metallocene complexes (I) of the present invention generally starts from 9,10-phenanthrenequinone or ring-substituted derivatives of this basic molecule. The 9,10-phenanthrenequinone or its derivative is then generally converted, as described in B Elliasson, J. Org. Chem. (1989), pages 171 to 175 and A. C. Cope, J. Am. Chem. Soc. (1956), pages 2547 to 2551, into the ketone precursor, viz. 2,3-dihydro-2-oxo-1H-cyclopenta [l]phenanthrene or its derivative, and finally by reduction of the keto group with organometallic compounds or hydrogen reductants into the hydrocarbon (III) or its tautomers.

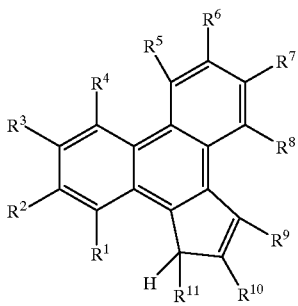

(III)

The metallocene complexes (I) of the present invention are generally obtained by deprotonating the hydrocarbon (III) using a strong, preferably organometallic, base, for example n-butyllithium, subsequently reacting it with a silylation reagent, preferably trimethylchlorosilane, and finally reacting the product with the transition metal halide, preferably a halide of transition group IV of the Periodic Table of the Elements, for example titanium tetrachloride, zirconium tetrachloride or hafnium tetrachloride.

The further conditions for these reactions are known to those skilled in the art and are described, for example, in J. Organomet. Chem. (1989), pages 359–370. Preference is given to carrying out the reactions in organic solvents such as diethyl ether, tetrahydrofuran, toluene or methylene chloride at a reaction temperature in the range from −78° C. to 150° C.

All the abovementioned reaction steps can be carried out without isolation and purification of the intermediates, but the intermediates are preferably isolated and purified.

As compounds B) capable of forming metallocenium ions, the catalyst systems can comprise open-chain or cyclic aluminoxane compounds.

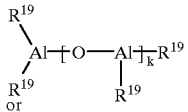 (IV)

or

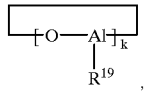 (V)

where $R^{19}$ is a $C_1$–$C_4$-alkyl group, preferably a methyl or ethyl group, and k is an integer from 5 to 30, preferably from 10 to 25.

The preparation of these oligomeric aluminoxane compounds is usually carried out by reacting a solution of trialkylaluminum with water and is described, inter alia, in EP-A 284 708 and U.S. Pat. No. 4,794,096.

The oligomeric aluminoxane compounds obtained in this way are generally in the form of mixtures of both linear and cyclic chain molecules of various lengths, so that k should be regarded as a mean value. The aluminoxane compounds can also be present in admixture with other metal alkyls, preferably with aluminum alkyls.

It has been found to be advantageous to use the metallocene complexes and the oligomeric aluminoxane compound in such amounts that the atomic ratio of aluminum from the oligomeric aluminoxane compound to the transition metal from the metallocene complexes is in the range from 10:1 to 106:1, preferably in the range from 10:1 to 104:1 and in particular from 20:1 to 9000:1.

Other compounds B) capable of forming metallocenium ions which can be used are coordination complexes selected from the group consisting of strong, uncharged Lewis acids, ionic compounds having Lewis acid cations and ionic compounds having Bronsted acids as cations.

As strong uncharged Lewis acids, preference is given to compounds of the formula VI $$M^1X^1X^2X^3 \quad (VI)$$

where $M^1$ is an element of main group III of the Periodic Table, in particular B, Al or Ga, preferably B, $X^1, X^2$ and $X^3$ are hydrogen, $C_1$–$C_{10}$-alkyl, $C_6$–$C_{15}$-aryl, alkylaryl, arylalkyl, haloalkyl or haloaryl each having from 1 to 10 carbon atoms in the alkyl radical and from 6 to 20 carbon atoms in the aryl radical or fluorine, chlorine, bromine or iodine, in particular haloaryls, preferably pentafluorophenyl.

Particular preference is given to compounds of the formula VI in which $X^1$, $X^2$ and $X^3$ are identical, preferably tris(pentafluorophenyl)borane. These compounds and processes for their preparation are known per se and are described, for example, in WO 93/3067.

Suitable ionic compounds having Lewis acid cations are compounds of the formula VII $$[(Y^{a+})Q_1Q_2 \ldots Q_z]^{d+} \quad (VII)$$

where

Y is an element of main groups I to VI or of transition groups I to VIII of the Periodic Table, $Q_1$ to $Q_z$ are singly negatively charged radicals such as $C_1$–$C_{28}$-alkyl, $C_6$–$C_{15}$-aryl, alkylaryl, arylalkyl, haloalkyl, haloaryl each having from 6 to 20 carbon atoms in the aryl radical and from 1 to 28 carbon atoms in the alkyl radical, $C_1$–$C_{10}$-cycloalkyl which may bear $C_1$–$C_{10}$-alkyl groups as substituents, halogen, $C_1$–$C_{28}$-alkoxy, $C_6$–$C_{15}$-aryloxy, silyl or mercaptyl groups, a is an integer from 1 to 6, z is an integer from 0 to 5 and d corresponds to the difference a - z, but d is greater than or equal to 1.

Particularly suitable cations are carbonium cations, oxonium cations and sulfonium cations and also cationic transition metal complexes. Particular mention may be made of the triphenylmethyl cation, the silver cation and the 1,1'-dimethylferrocenyl cation.

They preferably have noncoordinating counterions, in particular boron compounds as are also mentioned in WO 91/09882, preferably tetrakis(pentafluorophenyl)borate.

Ionic compounds having Bronsted acids as cations and preferably likewise noncoordinating counterions are mentioned in WO 93/3067; the preferred cation is N,N-dimethylanilinium.

It has been found to be particularly useful for the molar ratio of boron from the compound capable of forming metallocenium ions to transition metal from the metallocene complex to be in the range from 0.1:1 to 10:1, in particular in the range from 1:1 to 5:1.

The catalyst systems of the present invention can further comprise an organometallic compound of main group I, II or III of the Periodic Table as component C). Examples which may be mentioned are n-butyllithium, butyloctylmagnesium, triethylboron and preferably aluminum compounds.

The aluminum compounds can have, for example, the formula VIII $$AlR^{20}R^{21}R^{22} \quad (VIII),$$

where $R^{20}$ to $R^{22}$ are hydrogen, fluorine, chlorine, bromine, iodine or $C_1$–$C_{12}$-alkyl, preferably $C_1$–$C_8$-alkyl.

The radicals $R^{20}$ and $R^{21}$ are preferably identical and are $C_1$–$C_6$-alkyl such as methyl, ethyl, isobutyl or n-hexyl; $R^{22}$ is preferably hydrogen. An example which may be mentioned is diisobutylaluminum hydride.

In general, the molar ratio C):I) is in the range from 1:1 to 2000:1, preferably from 10:1 to 800:1.

In general, the molar ratio C):B) and here particularly C):aluminum IV, V is in the range from 0.001:1 to 10,000:1, preferably from 0.01:1 to 5000:1.

The catalyst systems of the present invention or at least one of their components A) to C), for example the metallocene complexes(I), can be used in unsupported or supported form.

Suitable support materials are, for example, silica gels, preferably those of the formula $SiO_2.bAl_2O_3$, where b is from 0 to 2, preferably from 0 to 0.5; ie. essentially aluminosilicates or silicon dioxide. The supports preferably have a particle diameter in the range from 1 to 200 µm, in particular from 30 to is 80 µm. Such products are commercially available, eg. as Silica Gel 332 from Grace.

Further supports are, inter alia, finely divided polyolefins, for example finely divided polypropylene or polyethylene, but also polyethylene glycol, polybutylene terephthalate, polyethylene terephthalate, polyvinyl alcohol, polystyrene, syndiotactic polystyrene, polybutadiene, polycarbonates or their copolymers.

The polymerization process of the present invention can be carried out essentially at from −78° C. to 150° C., preferably from 0 to 120OC; the polymerization temperature can also change over time and/or in space. It has been found to be advantageous to carry out the polymerization at from 60 to 150° C., preferably from 70 to 150° C. It was unexpected that at such high polymerization temperatures the activity of the catalyst system of the present invention, calculated as g of polymer/mol of transition metal×mol of monomer×h, and the molecular weight Mw of the polymer determined by means of GPC as defined below remains at a high level and that, in addition, the syndiotacticity of the polymer, measured by means of extraction with n-butanone, as already described, is still more than 40%, preferably more than 80%.

In general, the process of the present invention is carried out at a pressure of from 0.5 to 300 bar, preferably from 1 to 200 bar, in particular from 1 to 20 bar.

The process of the present invention can be carried out continuously or batchwise. Various process variants have been found to be useful.

In the polymerization in solution or in bulk monomer, the procedure is preferably to initially charge the monomer, preferably the above-defined vinylaromatic compound(II), in particular styrene, preferably to heat it to from 60 to 100° C. and then to add the compound B) capable of forming metallocenium ions, preferably methylaluminoxane or tris (pentafluorophenyl)borane or N,N-dimethylanilinium tetrakis(pentafluorophenyl)borate or a mixture of these components B) and, if desired, also the component C). The component A), if desired in a solvent, is then added. However, it is also possible to mix the metallocene complex A) beforehand with the compound B) capable of forming metallocenium ions and to introduce this mixture into the reactor. In general, polymerization is then carried out over a period of from 10 to 90 minutes and the polymerization is stopped by addition of methanol, the polymer is washed with methanol and dried at from 40 to 100° C.

The process of the present invention can also be carried out as a dispersion polymerization, as described in DE-A 195 42 356.

Examples of suitable dispersants are styrene-diene two-block copolymers or styrene-diene-styrene three-block copolymers. Preferred dispersion media are aliphatic hydrocarbons.

The dispersant is preferably used in an amount of from 1 to 10% by weight, based on the amount of vinylaromatic compounds used. It is advantageously added to the dispersion to be polymerized as a solution in the vinylaromatic monomer.

Suitable two-block copolymers can consist of a polymer block made up of styrene and a polymer block made up of butadiene, preferably 1,4-polybutadiene. The sum of the % by weight of the blocks made up of styrene and of butadiene is 100%, with the composition being able to vary. The styrene block can make up from 10 to 90% by weight, preferably from 20 to 80% by weight; the butadiene block can correspondingly make up from 90 to 10% by weight, preferably from 80 to 20% by weight. Also suitable are styrene-butadiene two-block copolymers which may be hydrogenated.

Examples of suitable styrene-diene-styrene three-block copolymers are those in which the diene block comprises polybutadiene or polyisoprene and where the diene block may be hydrogenated or unhydrogenated.

Two-block and three-block copolymers and processes for their preparation are known per se and are described, for example, in Thermoplastic Elastomers (1987), N. R. Liegge et al (ed.). Suitable copolymers are also commercially available, for example Kraton® grades (Shell).

Aliphatic hydrocarbons which are particularly suitable as dispersion medium are those having from 4 to 10 carbon atoms, for example butane, isobutane, pentane, hexane and heptane or hydrocarbon mixtures.

The preferred procedure in the process of the present invention is to dissolve the dispersant in the vinylaromatic compound, add the dispersion medium, preferably in an amount of from 1 to 10% by weight based on the vinylaromatic compound, then pass the olefinic compound through and add the metallocene catalyst system.

The polymerization can be stopped by addition of protic compounds such as methanol and the dispersion medium can be removed by increasing the temperature or, if desired, can be circulated.

Furthermore, the process of the present invention can be carried out as a suspension polymerization as described in DE-A 195 09 785. In this method, the monomer or mixture of monomers, preferably the vinylaromatic compound (II), is generally polymerized at a pressure of from 5 to 300 bar, preferably from 6 to 100 bar, in particular from 7 to 50 bar, in the presence of aliphatic $C_1$–$C_4$-hydrocarbons. Preference is given to linear or branched aliphatic $C_3$–$C_4$-hydrocarbons such as propane or isobutane and the catalyst system of the present invention or at least one of its components A), B) or C) is generally present in supported form, preferably on porous silica gel.

The process of the present invention can be carried out in various reactors. Suitable reactors are stirred vessels, kneaders and preferably extruders.

A particular embodiment of the process comprises carrying it out using a corotating, closely intermeshing and thus self-cleaning twin-screw extruder, preferably in one stage.

The reaction temperature is generally from −78 to 150° C., preferably from 0° to 150° C., in particular from 60 to 150° C. However, it is also possible for a temperature gradient of from 0 to 150° C. to be applied by means of heatable jackets around the reaction tube.

The extruder can have a plurality of individual zones which can be heated to different temperatures.

The external diameter of the corotating, preferably double flighted kneading and conveying elements of the twin-screw extruder is preferably in the range from 25 to 70 mm, in particular from 30 to 58 mm.

The free gaps between extruder barrel and screw element are in the range from 0.2 to 0.8 mm, in particular from 0.3 to 0.5 mm.

The rotational speed of the screws can be in the range from 3 to 500 revolutions per minute, preferably from 5 to 30 revolutions per minute.

The mean residence time in the extruder can be from 0.1 to 240 minutes, preferably from 2 to 20 minutes.

The mean residence time in the extruder can be regulated via the number of barrel sections. The number of barrel sections is preferably in the range from 6 to 20, in particular from 8 to 12.

Particular preference is given to using 10 barrel sections, where back-degassing takes place in the first barrel section, the starting materials are metered into the second barrel section, the barrel sections 3 to 8 are reaction sections, the barrel sections 9 and 10 can be heated at a different temperature and the barrel section 10 serves as discharge barrel.

The process is preferably carried out by mixing the vinylaromatic compound and, if desired, further monomers defined above, the compound B) capable of forming metallocenium ions and, if desired, the compound C) under an inert gas atmosphere and feeding them to the first barrel section of the extruder. In parallel thereto, a solution or suspension of the transition metal complex A) can likewise be fed to the first barrel section (zone).

As solvents or suspension media, mention may be made of cyclic and acyclic hydrocarbons such as butanes, pentanes, hexanes or heptanes, also aromatic hydrocarbons such as benzene, toluene or ethylbenzene and oxygen-containing hydrocarbons such as tetrahydrofuran, halogen-containing hydrocarbons such as dichloromethane or nitrogen-containing hydrocarbons such as N-methylpiperidine and also mixtures thereof.

The amount metered in is preferably selected such that from 500 to 2000 g/h of the mixture of vinylaromatic compound, if desired further above-defined monomers, components B) and, if used, C) are fed in and from 100 to 200 cm$^3$/h of the solution or suspension of the metal complex are fed in.

The polymerization is preferably carried out in the vinylaromatic compound and, if desired, further above-defined monomers as reaction medium, ie. in bulk.

The process is technically simple to carry out, high conversions are achieved and the risk of the outlet orifices of the extruder being blocked by polymer is low.

A further preferred embodiment comprises activating the reaction l mixture comprising vinylaromatic monomers II, if desired further above-defined monomers and the catalyst system comprising A), B) and, if desired, C) by premixing and subsequently polymerizing it in a mixing kneader.

The premixing is preferably carried out at a temperature at which the reaction mixture is still liquid and the polymerization does not commence. Depending on the components used for the reaction mixture, this temperature is in a range from −30 to +140° C., preferably from 0 to 70° C. and particularly preferably from to 30° C. Furthermore, in the activation according to the present invention, the premixing is preferably carried out with the residence time and the temperature being selected such that not only commencement of the polymerization reaction but also damage to the catalyst system are avoided despite sufficient mixing for the activation.

The activation by premixing the reaction mixture is advantageously carried out shortly or immediately before the polymerization reaction. The time between activation by premixing and polymerization is from 0 to 60 minutes, preferably from 0.01 to 45 minutes and particularly preferably from 0.1 to 30 minutes.

The premixing is preferably carried out essentially without commencement of a reaction.

The process is advantageously carried out without solvent. In a particularly preferred embodiment of the process, the monomers used initially act as solvent. In addition, it is advantageous to carry out the process in an inert gas atmosphere, for example of nitrogen or argon, if possible with exclusion of moisture. Hydrogen can also be metered into the inert gas stream.

The premixing is preferably carried out in such a way that no reaction occurs. Furthermore, it is advantageous for the polymers to be obtained in such a form that they can be further processed, for example extruded, essentially immediately after the polymerization. This is preferably the case when the polymerization in the process is driven to high yields and the polymer accordingly has a low residual monomer content. This residual monomer content is less than 10% by weight, preferably less than 5% by weight and particularly preferably less than 3% by weight, based on the weight of the polymer. The monomers still remaining in the polymer can be removed, for example, by distillation or by application of a vacuum. The process of the present invention is preferably carried out in a mixing-kneading reactor with an extruder connected downstream, without further work-up steps-, for example distilling off relatively large amounts of residual monomer which are obtained, in particular, in the case of low conversions, having to be carried out. The process therefore allows further processing of the polymer essentially immediately after its preparation.

If the polymerization of the present invention is carried out in the presence of branched monomers having at least two vinylaromatic functional radicals, for example tetrakis (4-vinylbenzyl)titanium or tetrakis(4-vinylbenzyl)silane, star polymers as described in the earlier German Patent Application 196 34 375.5-44 are generally obtained.

The linear polymers obtainable using the process of the present invention usually have a molecular weight Mw, determined by gel permeation chromatography at 135° C. in 1,2,4-trichlorobenzene as solvent against a polystyrene standard, in the range from 20,000 to $2\times10^6$, preferably in the range from 50,000 to $10^6$.

The syndiotacticity of the polymers obtainable using the process of the present invention is generally in the range from 30 to 100%, preferably in the range from 60 to 100%, in particular from 80 to 100% and very particularly preferably in the range from 90 to 100%. The syndiotacticity is determined by extracting a baked-out and weighed amount of polymer with 2-butanone for 24 hours, and drying and weighing the insoluble part of the polymer.

The melting point of the polymers of the present invention, determined by differential scanning calorimetry (DSC) in accordance with ISO 3146, is in the range from 250 to 285° C., preferably in the range from 260 to 280° C.

The polymerization process of the present invention can be carried out at high temperatures, and nevertheless gives polymers having a high molecular weight MW and a high degree of syndiotacticity.

EXAMPLES 2,3-Dihydro-2-oxo-1H-cyclopenta[I]phenanthrene was prepared as described by B. Elliasson, J. Org. Chem. (1989), pages 171 to 175 and A. C. Cope, J. Am. Chem. Soc. (1956), pages 2547 to 2551.

Preparation of 3-hydro-2-hydroxy-2-methyl-1H- cyclopenta [I]phenanthrene 8.83 ml of a 3 M solution of methylmagnesium bromide in diethyl ether (26.49 mmol) were added dropwise under protective gas to a suspension of 5.00 g of 2,3-dihydro-2-oxo-1H-cyclopenta[I]phenanthrene (21.19 mmol) in 20 ml of diethyl ether. After refluxing for 3 hours, the product was hydrolyzed by careful addition of 10 ml of 2 N hydrochloric acid. Extracting the mixture three times with diethyl ether, shaking the organic phase with saturated NaHSO$_3$ solution, saturated NaHCO$_3$ solution and a little water, drying over Na$_2$SO$_4$ and evaporating the solution gave a colorless solid.

Yield: 4.68 g (89%)

MS:

M$^+$: 248 m/e (33%)

M$^+$-CH$_3$CO: 205 m/e (100%)

NMR (CDCl₃, 600 MHz):

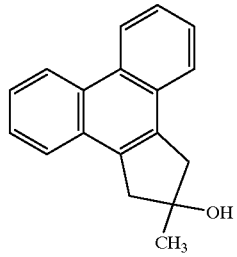

| Position | ¹H chemical shift | Multiplicity | Intensity | ¹³C chemical shift |
|---|---|---|---|---|
| 4,5 | 8.68–8.70 | m | 2 | 126.71 125.83 |
| 1–3, 6–8 | 7.77–7.79 | m | 2 | 124.76 123.22 |
|  | 7.59–7.63 | m | 4 | quat. C: 129.83 130.27 123.09 135.02 |
| OH(C—OH) | 1.98 | bs | 1 | 79.49 |
| CH₂ | 3.44 | 2d (J=15.8Hz) | 4 | 48.06 |
| Me | 1.66 | s | 3 | 28.46 |

Preparation of 1H-2-methylcyclopenta[I]phenanthrene 4.56 g of 3-hydro-2-hydroxy-2-methyl-1H-cyclopenta[I]phenanthrene (18.39 mmol) were dewatered by heating for one hour with 0.25 g of p-toluenesulfonic acid monohydrate in 300 ml of toluene on a water separator. The greenish blue solution changed to a reddish color after dilution with diethyl ether. The resulting solution was shaken with saturated sodium bicarbonate solution, dried over magnesium sulfate and evaporated. This gave a beige substance which could be purified by rapid filtration through a glass frit filled with flash silica gel (petroleum ether:ethyl acetate).

Yield: 4.02 g (95%)

MS:

M⁺: 230 m/e (100%)

M⁺-Me: 215 m/e (38%)

Elemental analysis:

$C_{18}H_{14}$

C: (calc.) 93.87 (found) 93.63

H: (calc.) 6.13 (found) 6.17

NMR (250 MHz, CDCl₃)

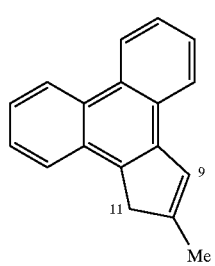

| Position | ¹H chemical shift | Multiplicity | Intensity | ¹³C chemical shift |
|---|---|---|---|---|
| 4,5 | 8.68–8.75 | m | 2 | 126.65 126.27 |
| 1–3, 6–8 | 8.10–8.13 | m | 1 | 125.51 125.14 |
|  | 7.93–7.95 | m | 1 | 124.60 124.39 |
|  | 7.53–7.65 | m | 4 | 123.61 123.43 |

-continued

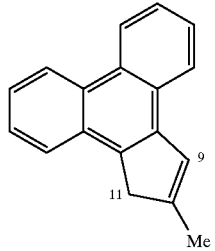

| Position | ¹H chemical shift | Multiplicity | Intensity | ¹³C chemical shift |
|---|---|---|---|---|
| 9 | 7.07 | bs | 1 | 123.25 quat. C: 127.50 128.30 129.64 130.19 137.05 140.22 |
| 11 | 3.74 | s | 2 | 42.95 |
| Me | 2.33 | bs | 3 | 16.94 |

Preparation of 1H-2-phenylcyclopenta[I]phenanthrene 1 g of 2,3-dihydro-2-oxo-1H-cyclopenta[I]phenanthrene (4.31 mmol) in 100 ml of toluene was added dropwise at 0° C. to 2 ml of a 3 M solution of phenylmagnesium bromide in diethyl ether (6 mmol). The mixture was allowed to come to room temperature and was stirred for 2 hours. After hydrolysis with saturated ammonium chloride solution, the mixture was extracted with diethyl ether, the organic phase was washed with saturated sodium chloride solution, dried over magnesium sulfate and evaporated to dryness. The residue was taken up in 100 ml of toluene and refluxed for 2 hours with 100 mg of p-toluenesulfonic acid. After addition of saturated sodium hydrogen carbonate solution, the mixture was extracted with diethyl ether, the organic phase was dried over magnesium sulfate and evaporated. After flash chromatography (petroleum ether:ethyl acetate=50:1) 1H-2-phenylcyclopenta[I]phenanthrene was obtained as colorless needles.

Yield: 0.45 g (36%)

MS:

$M^{*+}$: 292 m/e (100%)

$M^+$-Ph: 215 m/e (6%)

Elemental analysis:

$C_{23}H_{16}$

C: (calc.) 94.48 (found) 94.66

H: (calc.) 5.52 (found) 5.63

NMR ($CDCl_3$, 600 MHz):

| Position | $^1H$ chemical shift | Multiplicity | Intensity | $^{13}C$ chemical shift |
|---|---|---|---|---|
| 1 | 8.02 | d (J = 7.7 Hz) | 1 | 123.84 |
| 2 + 3 | 7.62–7.56 | m | 2 | 126.85, 125.25 |
| 4 | 8.68 | d (J = 8.2 Hz) | 1 | 123.51 |
| 5 | 8.72 | d (J = 7.1 Hz) | 1 | 123.34 |
| 6 + 7 | 7.66–7.64 | m | 2 | 125.87, 126.50 |
| 8 | 8.20 | d (J = 7.0 Hz) | 1 | 124.29 |
| 9 | 7.79 | s | 1 | 124.43 |
| 11 | 4.20 | s | 2 | 39.22 |
| o-Ph | 7.75 | d (J = 7.3 Hz) | 2 | 125.50 |
| m-Ph | 7.42 | t (J = 7.3 Hz) | 2 | 128.79 |
| p-Ph | 7.29 | t (J = 7.3 Hz) | 1 | 127.39 |
| quaternary C | | | | 146.43, 139.97 |
| | | | | 137.74, 136.03 |
| | | | | 130.33, 129.48 |
| | | | | 128.93, 127.56 |

General Method of Preparing 1-trimethylsilylcyclopenta[I]-phenanthrenes

The respective cyclopenta[I]phenanthrene (10 mmol) was initially charged in 20 ml of THF and admixed while cooling in ice with 10 mmol of n-BuLi as a 1.6 M solution in hexane. The mixture was allowed to come to room temperature and was stirred overnight. The dark green solution was evaporated to dryness.

1-Trimethylsilylcyclopenta[I]phenanthrene

Yield: 2.05 g (90%), yellow oil

MS:

$M^+$: 288 m/e (30%)

$M^+$-TMS: 215 m/e (10%)

TMS: 73 m/e (100%)

$^1H$ NMR ($CDCl_3$, 250 MHz):

| Position | $^1H$ chemical shift | Multiplicity | Intensity |
|---|---|---|---|
| Phenanthrene skeleton | 8.75–8.70 | m | 2 |
| | 8.26–8.22 | m | 1 |
| | 8.01–7.97 | m | 1 |
| +Cp-H | 7.65–7.53 | m | 5 |
| Cp-H | 6.89–6.86 | m | 1 |
| Cp-H | 4.35 | bs | 1 |
| TMS | −0.05 | s | 9 |

1-Trimethylsilyl-2-methylcyclopenta[I]phenanthrene

Yield: 2.60 g (86%), yellow oil

MS:

$M^+$: 302 m/e (40%)

$M^+$-TMS: 228 m/e (10%)

TMS: 73 m/e (100%)

$^1H$ NMR ($CDCl_3$, 250 MHz):

| Position | $^1H$ chemical shift | Multiplicity | Intensity |
|---|---|---|---|
| Phenanthrene skeleton | 8.71–8.64 | m | 2 |
| | 8.15–8.12 | m | 1 |
| | 7.88–7.85 | m | 1 |
| | 7.63–7.48 | m | 4 |
| Cp-H | 7.13 | s | 1 |
| Cp-H | 4.15 | s | 1 |
| Me | 2.35 | s | 3 |
| TMS | −0.08 | s | 9 |

1-Trimethylsilyl-2-phenylcyclopenta[I]phenanthrene

Yield: 2.76 g (76%), beige solid

MS:

$M^+$: 364 m/e (20%)

$M^+$-TmS: 291 m/e (7%)

TMS: 73 m/e (65%)

$^1H$ NMR ($CDCl_3$, 250 MHz):

| Position | $^1H$ chemical shift | Multiplicity | Intensity |
|---|---|---|---|
| Phenanthrene skeleton | 8.73–8.68 | m | 2 |
| | 8.27–8.24 | m | 1 |
| | 8.04–8.00 | m | 1 |
| +Ph-H | 7.68–7.53 | m | 6 |
| Cp-H | 7.70 | s | 1 |
| Ph-H | 7.45–7.39 | m | 2 |
| Ph-H | 7.32–7.25 | m | 1 |
| Cp-H | 4.91 | s | 1 |
| TMS | −0.30 | s | 9 |

General Method of Preparing cyclopenta[I]phenanthrenetitanium trichloride and Derivatives 1-Trimethylsilylcyclopenta[I]phenanthrene or its 2-methyl or 2-phenyl derivative (batch size corresponding to the amounts obtained above) was dissolved in 30 ml of methylene chloride and admixed at 0° C. with an equimolar amount of titanium tetrachloride. The orange solution immediately became reddish brown. After stirring for 4 hours at room temperature, the mixture was cooled to −30° C. overnight. After decanting off the solution, the product could be obtained as a dark red solid. The yield could be considerably improved by concentrating the mother liquor and cooling again.

The numbering of the following cyclopenta[I] phenanthrenes in the NMR tables is according to the general scheme:

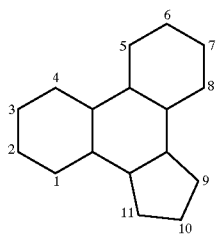

Cyclopenta[I]phenanthrenetitanium trichloride
  Yield: 1.76 g (53%), red solid
  MS:
  M$^+$: 370 m/e (7%)
  M$^+$-Cl: 333 m/e (1%)
  Lig-H: 215 m/e (100%)
  Elemental analysis:
  $C_{17}H_{11}TiCl_3$
  C: (calc.) 55.26 (found) 54.77
  H: (calc.) 3.00 (found) 3.22
  NMR (CDCl$_3$, 600 MHz): $^1$H, $^{13}$C

| Position | $^1$H chemical shift | Multiplicity | Intensity | $^{13}$C chemical shift |
|---|---|---|---|---|
| 4,5 | 8.56 | d (J = 8.0 Hz) | 2 | 124.07 |
| 2,3,6,7 | 7.73–7.67 | m | 4 | 128.32, 130.07 |
| 1,8 | 8.23 | d (J = 7.4 Hz) | 2 | 125.47 |
| 9,11 | 7.62 | d (J = 3.3 Hz) | 2 | 115.42 |
| 10 | 7.25 | t (J = 3.3 Hz) | 1 | 123.09 |
| quaternary C | | | | 131.17, 131.10, 127.57, ~126 |

2-Methylcyclopenta[I]phenanthrenetitanium trichloride
  Yield: 1.75 g (53%), red solid
  MS:
  M$^+$: 384 m/e (8%)
  M$^+$-Cl: 347 m/e (2%)
  M$^+$-2Cl: 311 m/e (2%)
  MeLig-H: 229 m/e (100%)
  Elemental analysis:
  $C_{18}H_{13}TiCl_3$
  C: (calc.) 56.37 (found) 55.98
  H: (calc.) 3.42 (found) 3.54
  NMR (CDCl$_3$, 600 MHz): $^1$H, $^{13}$C

| Position | $^1$H chemical shift | Multiplicity | Intensity | $^{13}$C chemical shift |
|---|---|---|---|---|
| 4,5 | 8.54 | d (J = 7.9 Hz) | 2 | 124.02 |
| 2,3,6,7 | 7.71–7.65 | m | 4 | 128.25, 129.80 |
| 1,8 | 8.18 | d (J = 7.6 Hz) | 2 | 125.13 |
| 9,11 | 7.47 | s | 2 | 115.85 |
| Me | 2.73 | s | 3 | 18.87 |
| quaternary C | | | | 131.64, 130.89, 128.07, 125.19 |

2-Phenylcyclopenta[I]phenanthrenetitanium chloride
  Yield: 2.23 g (66%), red solid

MS:

M$^+$: 446 m/e (6%)

PhLig-H: 291 m/e (100%)

Elemental analysis:

$C_{23}H_{15}TiCl_3$

C: (calc.) 61.99 (found) 61.67

H: (calc.) 3.39 (found) 3.80

NMR (CDCl$_3$, 600 MHz): $^1$H, $^{13}$C

| Position | $^1$H chemical shift | Multiplicity | Intensity | $^{13}$C chemical shift |
|---|---|---|---|---|
| 4,5 | 8.57 | d (J = 7.7 Hz) | 2 | 124.46 |
| 2,3,6,7 | 7.7–7.69 | m | 4 | 128.66, 130.36 |
| 1,8 | 8.29 | d (J = 7.4 Hz) | 2 | 125.33 |
| 9,11 | 8.03 | s | 2 | 110.96 |
| o-Ph | 7.99 | d (J = 7.4 Hz) | 2 | 127.03 |
| m-Ph | 7.54 | t (J = 7.4 Hz) | 2 | 129.47 |
| p-Ph | 7.46 | t (J = 7.4 Hz) | 1 | 130.80 |

Styrene Polymerizations

In a 300 ml Schlenk vessel, 50 ml of toluene, 5 ml of styrene hich had been freshly distilled over calcium hydride and 6 ml of ethylaluminoxane (MAO: 1.69 M in toluene) were heated to the desired polymerization temperature and stirred for 10 minutes. The titanium catalyst (2.5 μmol, 1 ml of a 2.5 mM solution in toluene) was added by means of a syringe and the reaction solution was stirred for from 10 to 20 minutes (Al:Ti=4000:1). The mixture was hydrolyzed by addition of 10% of HCR in methanol, the precipitated polystyrene was filtered off, washed with further methanol and dried overnight at 100° C. Atactic material was removed by Soxhlett extraction with 2-butanone for 24 hours. The polymer was then again dried overnight at 100° C. and weighed to determine the syndiotactic content. The polymerization results are shown in the following table.

TABLE

Polymerization of styrene using various metallocene/methylalumninoxane catalysts

| | 50° C.[6] | | | | 75° C. | | | | 100° C. | | | |
|---|---|---|---|---|---|---|---|---|---|---|---|---|
| Metallocene[1] | A[2] | SY[3] | $M_w$[4] | $T_m$[5] | A | SY | $M_w$ | $T_m$ | A | SY | $M_w$ | $T_m$ |
| 2-Methylcyclopenta[I]phenanthrenetitanium trichloride R = CH$_3$ | 10 | 83 | 12.3 | 270.2 | 26 | 89 | 7.4 | 267.5 | 24 | 82 | 2.9 | 259.6 |

TABLE-continued

Polymerization of styrene using various metallocene/methylalumninoxane catalysts

| Metallocene[1] | 50° C.[6] | | | | 75° C. | | | | 100° C. | | | |
|---|---|---|---|---|---|---|---|---|---|---|---|---|
| | A[2] | SY[3] | $M_w$[4] | $T_m$[5] | A | SY | $M_w$ | $T_m$ | A | SY | $M_w$ | $T_m$ |
| 2-Phenylcyclopenta[I]phenanthrenetitanium trichloride R = $C_6H_5$ | 40 | 85 | 27.7 | 267.8 | 75 | 92 | 13.0 | 265.2 | 45 | 90 | 5.8 | 264.9 |

1)
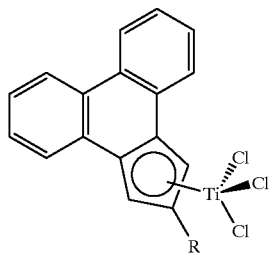

[2] A = Activity [× $10^7$ g of polystyrene/(mol of Ti × mol of styrene × h)]
[3] Syndiotacticity [% by weight of material insoluble in 2-butanone]
[4] Molecular weight (weight average) [× $10^4$] determined by GPC
[5] Melting point [° C.] determined by DSC
[6] Polymerization temperature

We claim:
1. A process for preparing polymers based on monomers having a C=C double bond by homopolymerization or copolymerization of these monomers in the presence of a catalyst system comprising a metallocene complex A) and a compound B) capable of forming metallocenium ions and, optionally, an organometallic compound of main group I, II or III of the Periodic Table of the Elements C), wherein the metallocene complex A) used is a compound of the formula (I)

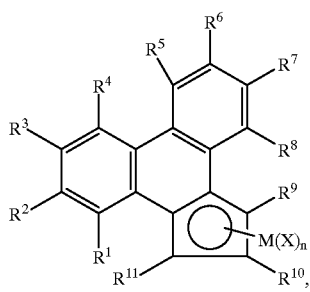

where the substituents and indices have the following meanings:
$R^1$ to $R^{11}$ are hydrogen, $C_1$–$C_{10}$-alkyl, 5- to 7-membered cycloalkyl which may in turn bear $C_1$–$C_6$-alkyl groups as substituents, $C_6$–$C_{15}$-aryl or arylalkyl, where two adjacent radicals $R^1$ to $R^8$ may together form a cyclic group having from 4 to 15 carbon atoms, or $Si(R^{12})_3$, where $R^{12}$ is $C_1$–$C_{10}$-alkyl, $C_6$–$C_{15}$-aryl or $C_3$–$C_{10}$-cycloalkyl, M is a metal of transition groups III to VI of the Periodic Table of the Elements or a metal of the lanthanide series, X are identical or different and are hydrogen, halogen, $C_1$–$C_{10}$-alkyl, $C_6$–$C_{15}$-aryl, $C_1$–$C_{10}$-alkoxy or $C_6$–$C_{15}$-aryloxy and n is 1, 2, 3, 4 or 5, where n corresponds to the valence of M minus 1.

2. A process for preparing polymers as claimed in claim 1, wherein the polymers are partially crystalline, have syndiotactic structural units and the monomers used are vinylaromatic compounds of the formula (II)

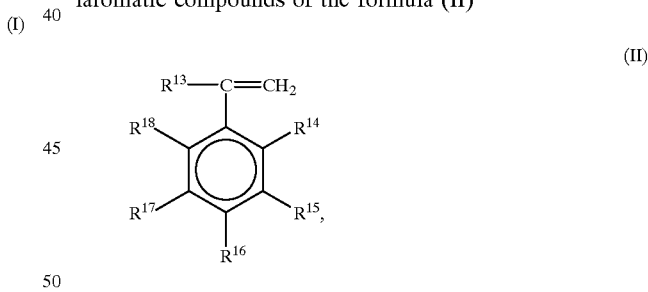

where the substituents have the following meanings:

$R^{13}$ is hydrogen or $C_1$–$C_4$-alkyl, $R^{14}$ to $R^{18}$ are, independently of one another, hydrogen, $C_1$–$C_{12}$-alkyl, $C_6$–$C_{18}$-aryl, halogen or two adjacent radicals together form a cyclic group having from 4 to 15 carbon atoms, and, optionally, additionally $C_2$–$C_{20}$-alkenes or $C_3$–$C_{20}$-cycloalkenes.

3. A catalyst system which is suitable for polymerizing monomers having a C=C double bond and comprises as active constituents A) a metallocene complex of the formula (I)

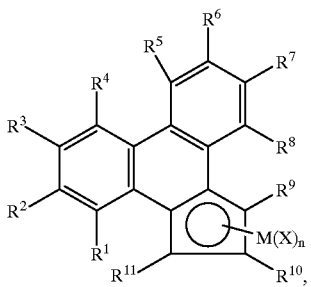

where the substituents and indices have the following meanings:

R$^1$ to R$^{11}$ are hydrogen, C$_1$–C$_{10}$-alkyl, 5- to 7-membered cycloalkyl which may in turn bear C$_1$–C$_6$-alkyl groups as substituents, C$_6$–C$_{15}$-aryl or arylalkyl, where two adjacent radicals RI to R$^8$ may together form a cyclic group having from 4 to 15 carbon atoms, or Si(R$^{12}$)$_3$, where R$^{12}$ is C$_1$–C$_{10}$-alkyl, C$_6$–C$_{15}$-aryl or C$_3$–C$_{10}$-cycloalkyl, M is a metal of transition groups III to VI of the Periodic Table of the Elements or a metal of the lanthanide series, X are identical or different and are hydrogen, halogen, C$_1$–C$_{10}$-alkyl, C$_6$–C$_{15}$-aryl, C$_1$–C$_{10}$-alkoxy or C$_6$–C$_{15}$-aryloxy and n is 1, 2, 3, 4 or 5, where n corresponds to the valence of M minus 1, B) a compound capable of forming metallocenium ions and, optionally, C) an organometallic compound of main group I, II or II of the Periodic Table of the Elements.

4. A catalyst system as claimed in claim 3, wherein M is a metal of transition group IV of the Periodic Table of the Elements.

5. A metallocene complex of the formula (I)

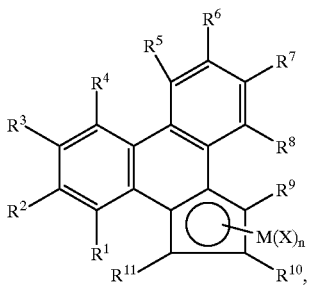

where the substituents and indices have the following meanings:

R$^1$ to R$^{11}$ are hydrogen, C$_1$–C$_{10}$-alkyl, 5- to 7-membered cycloalkyl which may in turn bear C$_1$–C$_6$-alkyl groups as substituents, C$_6$–C$_{15}$-aryl or arylalkyl, where two adjacent radicals R$^1$ to R$^8$ may together form a cyclic group having from 4 to 15 carbon atoms, or Si(R$^{12}$)$_3$, where R$^{12}$ is C$_1$–C$_{10}$-alkyl, C$_6$–C$_{15}$-aryl or C$_3$–C$_{10}$-cycloalkyl, M is a metal of transition groups III to VI of the Periodic Table of the Elements or a metal of the lanthanide series, X are identical or different and are hydrogen, halogen, C$_1$–C$_{10}$-alkyl, C$_6$–C$_{15}$-aryl, C$_1$–C$_{10}$-alkoxy or C$_6$–C$_{15}$-aryloxy and n is 1, 2, 3, 4 or 5, where n corresponds to the valence of M minus 1.

6. Cyclopenta[I]phenanthrenetitanium trichloride, 2-methylcyclopenta[I]phenanthrenetitanium trichloride and 2-phenylcyclopenta[I]phenanthrenetitanium trichloride.

7. A polymer based on monomers having a C=C double bond, obtainable by homopolymerization or copolymerization of these monomers in the presence of a catalyst system comprising as active constituents a metallocene complex A) and a compound B) capable of forming metallocenium ions and, optionally, an organometallic compound of main group I, II or III of the Periodic Table of the Elements C), wherein the metallocene complex A) used is a compound of the formula (I)

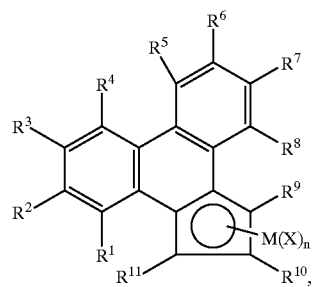

where the substituents and indices have the following meanings:

R$^1$ to R$^{11}$ are hydrogen, C$_1$–C$_{10}$-alkyl, 5- to 7-membered cycloalkyl which may in turn bear C$_1$–C$_6$-alkyl groups as substituents, C$_6$–C$_{15}$-aryl or arylalkyl, where two adjacent radicals R$^1$ to R$^8$ may together form a cyclic group having from 4 to 15 carbon atoms, or Si(R$^{12}$)$_3$, where R$^{12}$ is C$_1$–C$_{10}$-alkyl, C$_6$–C$_{15}$-aryl or C$_3$–C$_{10}$-cycloalkyl, M is a metal of transition groups III to VI of the Periodic Table of the Elements or a metal of the lanthanide series, X are identical or different and are hydrogen, halogen, C$_1$–C$_{10}$-alkyl, C$_6$–C$_{15}$-aryl, C$_1$–C$_{10}$-alkoxy or C$_6$–C$_{15}$-aryloxy and n is 1, 2, 3, 4 or 5, wherein n corresponds to the valence of M minus 1.

8. A fiber, film or molding comprising a polymer as claimed in claim 7.

* * * * *

UNITED STATES PATENT AND TRADEMARK OFFICE
CERTIFICATE OF CORRECTION

PATENT NO. : 6,284,851 B1
DATED : September 4, 2001
INVENTOR(S) : Wuensch et al.

It is certified that error appears in the above-identified patent and that said Letters Patent is hereby corrected as shown below:

Column 21, claim 3,
Line 22, "RI" should be -- $R^1$ --.

Column 22, claim 5,
Line 2, "Si($R^{12}$)3" should be -- Si($R^{12}$)$^3$ --.

Signed and Sealed this

Twenty-sixth Day of February, 2002

Attest:

JAMES E. ROGAN
*Attesting Officer*  *Director of the United States Patent and Trademark Office*